US00RE40155E

(19) United States
(12) Reissued Patent
Margolin

(10) Patent Number: US RE40,155 E
(45) Date of Reissued Patent: Mar. 18, 2008

(54) METHODS FOR TREATMENT OF BENIGN AND MALIGNANT TUMORS, INCLUDING LYMPHOMAS, LEUKEMIAS, AND LEIOMYOMAS

(76) Inventor: Solomon B Margolin, 6723 Desco Dr., Dallas, TX (US) 75225

(21) Appl. No.: 09/724,378

(22) Filed: Nov. 27, 2000

Related U.S. Patent Documents

Reissue of:
(64) Patent No.: 6,114,353
Issued: Sep. 5, 2000
Appl. No.: 09/239,211
Filed: Jan. 28, 1999

U.S. Applications:
(63) Continuation-in-part of application No. 09/162,011, filed on Sep. 28, 1998, now Pat. No. 6,090,822, which is a continuation-in-part of application No. 08/913,202, filed on Sep. 3, 1997, now abandoned, which is a continuation-in-part of application No. PCT/US96/02737, filed on Mar. 4, 1996, said application No. 09/239,211, filed on Jan. 28, 1999, is a continuation-in-part of application No. 08/397,962, filed on Mar. 3, 1995, now abandoned.

(51) Int. Cl.
*A61K 31/47* (2006.01)

(52) U.S. Cl. ..... 514/313; 514/334; 514/336
(58) Field of Classification Search ..... 514/313, 514/334, 336, 341, 342, 345
See application file for complete search history.

(56) References Cited

U.S. PATENT DOCUMENTS 4,042,699 A * 8/1977 Gadekar ..... 514/345
4,052,509 A * 10/1977 Gadekar ..... 514/345
5,962,478 A * 10/1999 Margolin ..... 514/345

FOREIGN PATENT DOCUMENTS

WO WO 96/27374 9/1996

OTHER PUBLICATIONS

Ross, Russell, PhD. Medical Progress; The Pathogenesis of Athersclerosis—An Update; The New England Journal of Medicine vol. 314, No. 8, pp. 488, 493, 494; Department of Patholology, University of Washington School of Medicine, Seattle, Washington; Feb. 20, 1986.*

Saven, Alan, M.D., et al.; Brief Communications, 2–Chlorodeoxyadenosine–induced Complete Remissions in Langerhans–Cell Histiocytosis, pp. 430–432; Reprint from Annals of Internal Medicine, vol. 121, No. 6, Sep. 15, 1994.*

Schwartz, Stephen M., et al; Remodeling: How Vessels Narrow, Clinical Trials and Remoldeling; pp. 128–131; University of Washington, Seattle, WA; Massachusetts General Hospital, Boston, MA; and ZymoGenetics, Inc., Seattle WA. 1996.*

Waltenberger, Johannes, M.D., Current Perspectives, Modulation of Growth Factor Action, Implications for the Treatment of Cardiovascular Diseases; Circulation, pp. 4083–4094; vol. 96, No. 11, Department of Internal Medicine II (Cardiology); Ulm University Medical Center, Ulm Germany; Dec. 2, 1997.*

(Continued)

*Primary Examiner*—Christopher S. F. Low
*Assistant Examiner*—Shirley V. Gembeh
(74) *Attorney, Agent, or Firm*—John H. Crozier

(57) ABSTRACT

In a preferred embodiment, drugs having chemotherapeutic properties which are useful against certain neoplastic disorders with wide safety margins as evidenced by their low toxicity, and molecular actions. Such drugs include as active ingredient(s) one or more N-substituted 2-(1H) pyridone(s) and/or N-substituted 3-(1H) pyridone(s). The compositions of this invention are novel as anti-neoplastic drugs, namely [as an agent for treating leukemias, lymphomas, and leiomyomas] *as agent(s) for treating benign and malignant tumors, including lymphomas, leukemias, and leiomyomas.*

4 Claims, 4 Drawing Sheets

Inhibition by Pirfenidone of Proliferation of Human Pro-Myelocytic Leukemia (HL-60) Cells

OTHER PUBLICATIONS

Copy of Brochure for Leustatin.RTM. (cladribine) Injection; Ortho Biotech, Raritan, New Jersey, Dec. 1996.*

Lee et al., Pirfenidone: A Novel Pharmacological Agent That Inhibits Leimomyoma Cell Proliferation and Collegen Production, 1998, US, J. Clin. Endocrinal Metab 83: 219–223.

* cited by examiner

*P<0.05
**P<0.01

METHODS FOR TREATMENT OF BENIGN AND MALIGNANT TUMORS, INCLUDING LYMPHOMAS, LEUKEMIAS, AND LEIOMYOMAS

Matter enclosed in heavy brackets [ ] appears in the original patent but forms no part of this reissue specification; matter printed in italics indicates the additions made by reissue.

This application is a CIP of Ser. No. 09/162,011 filed Sep. 28, 1998 which is a CIP of Ser. No. 08/913,202 filed Sep. 3, 1997 ABN., which is a CIP of PCT/US96/02737 filed Mar. 4, 1996 which is a CIP of Ser. No. 08/397,962 filed Mar. 3, 1995 ABN.

BACKGROUND OF THE INVENTION

1. Field of the Invention

The present invention relates to medical compositions and methods for the chemotherapeutic treatment of lymphomas, leukemias, and leiomyomas generally and, more particularly, to compositions comprising one or more N-substituted 2(1H) pyridones and/or one or more N-substituted 3(1H) pyridones as active ingredient(s). The selected compounds nay be used alone or as an adjunct to other forms of neoplastic therapy including surgery, other chemotherapeutic compounds, radiation therapy, and immunotherapeutic agents.

2. Background Art

The causes of leukemias and leiomyomas are poorly understood, are complex, and involve interplay between the basic genetic material in the nucleus of cells. An abnormal reaction of cellular genetic DNA to internal or external factors can create a new deviation in the cell genetic code, or in the genetic DNA generated communication proteins which creates neoplastic perturbations in the transcription process governing the specific cell cycle stages of otherwise normal cell division, and proliferation.

Cell proliferation is defined as the increase in number of cells resulting from completion of the cell cycle, as contrast to growth, which is the increase in the individual cell mass.

Extracellular or intracellular factors can determine whether a quiescent cell will begin to proliferate and also whether a normal proliferating cell in phase G1 will begin to cycle or will revert to quiescence. After cells enter into the S Phase, cell-cycle events become largely independent of prior extracellular factors., while they go on to divide and produce two daughter cells.

Among the carcinogenic factors of external origin, acting internally, are physical carcinogens such as ionizing or ultraviolet radiation, and the presence of foreign substances such as asbestos. Carcinogenic substances acting internally include various chemicals, natural or man-made, which can effect directly or indirectly cell DNA to elicit intracellular oncogenic events. In addition biological substances such as bacteria, viruses, parasites, hormones and cytokines have been implicated in mammalian carcinogenesis.

In *benign and malignant tumors including* lymphomas, leukemias and leiomyomas, the control of proliferation is deranged. After induction of altered proliferation control, deranged cell differentiation is initiated in phase G1, and is a hallmark of neoplastic cells (Pardee. A. B., Science, Nov. 3, 1989, p.603).

Neoplasms are manifest when the normal progression of the orderly relationship between cell division and cell differentiation malfunctions. With the usual cell division sequence in normal cells, the proliferation of cells is restricted to non-differentiated stem cells which ordinarily differentiate and reproduce to provide a replacement for aged dying cells.

Neoplasms arising from lympho-hematopoietic origin may be identified as leukemias, lymphomas, leiomyomas, etc.

The term "anti-neoplastic" or "anti-tumor" refers herein to the (a) chemotherapeutic inhibition of arrest of the growth, and (b) the destruction of mammalian benign [.] *(for example leiomyomas) and/*or malignant tissues (such as leukemias[.] *or* lymphomas), [and leiomyomas] found in various organs and tissues of the body.

Although most tissues and organs of the human body may become neoplastic, the basic processes leading to diverse tumors appear to be quite similar. Normal cells proliferate or reproduce in rigorous compliance with programmed guidance from parental or adjacent cells. Such unceasing, disciplined instruction ensures that each tissue maintains a size, architecture and function appropriate to the body's needs.

Neoplastic cells, in distinct contrast, become unresponsive to the usual controls of parental or adjacent cells with respect to proliferation, architecture and/or function. These neoplastic cells frequently (a) migrate from the site where they began, (b) invade nearby tissues, and (c) travel through the blood and lymphatic circulatory systems to form neoplastic lesions at distant sites in the body. These lesions become lethal when they disrupt the normal function of other tissues or organs essential for the patient survival.

Multiple genetic changes occur during the transformation of normal cells into neoplastic cells. This is facilitated in neoplastic cells by loss of fidelity in the processes that replicate, repair, and segregate the genome structure. Advances in our understanding of the cell cycle reveal how fidelity is normally achieved by the coordinated activity of cyclin-dependent kinases, checkpoint controls, and repair pathways, and how this fidelity can be abrogated by specific genetic changes. The recognition of molecular mechanisms for cellular transformation may help identify the mechanisms by which chemotherapeutic compounds are useful in the treatment of neoplastic diseases (Hartwell, L. and Kasten, M., 1994, Science. 266:1821–1828).

Control systems enforcing interdependency in the cell cycle are called "checkpoints." Elimination of checkpoints can result in cell death, infidelity in the distribution chromosomes or other cellular organelles, or increased susceptibility to external perturbations such as DNA damaging agents. Such perturbations can result in neoplastic transformation of cells and tissues (Hartwell, L. and Weinert, T., 1989, Science, 246:629–634).

The cell-type-specific expression of most genes is determined at the transcription level. Transcription factors are involved in the control of the process. To understand the basis of this regulation, it has become important to analyze the control of transcription factors themselves. A variety of transcriptional, translational, and post-translational mechanisms have been described. The most direct way for a cell to regulate the abundance of a factor is to adjust the production of the mRNA encoding it. Thus far, the control of many cell-type and tissue-specific transcription factors has been found to occur at the transcription level (Falvey, E., and Schibler, U., FASEB J., 1991, 5:309–314).

Recent studies indicate that extracellular signals often effect cell proliferation and differentiation by modulating intracellular transcription factor activity via protein phosphorylation cascades, which involves the transduction systems used to transmit information (signals) from the cell surface to the transcription machinery of the cell nucleus (Karin, M., 1992, FASEB J. 6:2581–2590).

Cell nuclear transcription factors regulate tissue and stimulus-specific gene expression through their ability to integrate extracellular signals at the nucleus. Several human diseases, including neoplasias, cardiovascular disease, and neurological and autoimmune disorders, result from aberrations in the expression of genes regulated by these transcription factors (Manning, A. Gonzales, R., and Bennett, B., Expert Opin. Ther. Pat., 1997, 7:225–231).

Normally, the body's tissues prevent excessive proliferation of cells by depriving them of excessive amounts of growth-stimulating factors, or by flooding the cells with antiproliferative factors derived from adjacent or parental cells which block the actions of the growth stimulating factors.

Certain cellular proteins, through their intrinsic ability to regulate a host of other genes involved in the control of cell proliferation, can reorganize and redirect a cell's normal or abnormal fate. Thus, the loss of these growth controlling genes by deletion or mutation is a common occurrence in neoplasias (Lozano, G. and Hulboy, D. L., Methods (San Diego) 1995, 8:215–224.)

Some cell cycle derangements stem from extracellular influences. Many neoplasia causing oncogenes, for example, turn out to encode components of the pathways through which various growth factor signals feed into the cell cycle to stimulate cell division. This is an important demonstration that the protein encoded by the p53 tumor suppresser gene inhibits cell growth by turning on the production of a specialized protein that blocks the cell cycle. The intracellular gene encoding one component of the cell cycle machinery, a protein called cyclin D1, as well as several others, are oncogene candidates. A significant amount of experimental evidence indicates that excess cyclin D1 causes neoplasias, but additional data suggest that several gene changes are implicated in the transformation of normal cells into a neoplastic configuration. For example, a hallmark of normal healthy cells is their ability to differentiate, but neoplastic cells cannot differentiate due the blockade of this response via the combined action of cyclins D2 and D3 (Marx, J., 1994, Science, 263:319–321).

Other recent data strongly suggest that deregulation of the restriction checkpoints in the cell-cycle G-1 phase is required for the transition to neoplastic disarray as seen in neoplasias (Strauss, M.; Lucas, J.; Bartek, J. Nat. Med. (N.Y.), 1995 1:1245–1246).

Mitogenic stimulation of normal cells initiates a sequence of events leading to activation of cyclin-dependent kinases, phosphorylation of Rb, and subsequent entry into of the cell into the S phase. Many types of neoplasms have lost sensitivity to the growth-inhibitory actions of TGF-beta-1, and this may derive from dysregulated expression of cyclin, cdk, and cdk inhibitor genes (Satterwhite, D. and Moses, H., 1994–1995 (Publ. 1995), Invasion Metastasis, 14:309–318).

Large T-antigen expression in human fibroblasts selectively uncouples cyclin D1 from cdk4, and subsequent immortalization of these cells results in additional changes in the cyclin D-dependent cell cycle regulatory pathways (Peterson, S. et al., 1995, Cancer Res., 55:4651–4657).

Representative Neoplasms of the Immune System

Each neoplasm of the immune system exhibits a distinct clinical and pathologic character, yet these disorders share a number of common features. Systemic symptoms of fever, night sweats, and weight loss may be present and are associated with advanced stages of the disease. These tumors usually appear in one or more organs of the hematopoietic system (lymph nodes, spleen, liver, bone marrow). If untreated, fatal dissemination to all of these organs, as well as other sites occurs.

Chronic myeloid leukemia (CML) usually presents clinically in a chronic phase of variable duration, after which a fatal condition similar to acute leukemia (blast crisis) develops. The problem of initial therapy for chronic phase CML is that current conventional therapy offers little chance of long-term survival of the patient with no chance of cure, whereas an agent that offers superior survival and a chance of cure is very toxic and expensive (Kattan, M., et al., Ann. Intern. Med., 1996; 125:541–548).

The disease is characterized by overproduction of granulocytic cells (especially neutrophilic types), leading to marked splenomegaly, and very high white blood cell counts. Rises in basophils and thrombocytosis occur frequently.

Inhibition of proliferation by pirfenidone of human uterine leiomyomas or fibroid cells in vitro. According to the literature, leiomyomas are the most common pelvic tumors in women with a reported incidence of 20% or more (Merrill, J., Creasman, W. 1990, "Danforth's Obstetrics and Gynecology," Scott, J., et al., eds., 6th edition. Philadelphia. Lippincott, pp. 1023–1039). Most common symptoms associated with these benign tumors are excessive abnormal uterine bleeding, pelvic pain, infertility and increased urinary frequency. Consequently, the presence of leiomyomas is the leading cause for hysterectomy in the United States (Wilcox, L. et al., 1994, Hystersectomy in the United States, 1990, Obstet. Gynecol. 83:549–555).

The majority of chemotherapeutic neoplasia agents in current clinical practice are toxic compounds and exert their greatest anti-neoplasia effect when employed at the maximum tolerated dose. With these chemotherapeutic agents, toxic actions to normal tissue can greatly limit the amount that can be safely administered. To date, the most commonly utilized agents are only partially selective in their toxicity. Thus, they are damaging to both normal and neoplastic cells. These agents disrupt major intracellular systems such as DNA synthesis and essential enzymes systems. Nevertheless treatment of neoplastic disease is predicated on exploiting the small differences between healthy normal cells and neoplastic cells.

Accordingly, it is a principal object of the present invention to provide compositions for the inhibition or arrest of the growth or for the destruction of mammalian benign (*for example leiomyomas*) and/*or* malignant tumors [lymphomas,] (for example leiomyomas[,] and leukemias, *etc.*).

It is a further object of the present invention to provide such compositions that provide a means of (1) arresting the proliferation of and (2) then killing the abnormal cells of neoplastic tissue without serious or fatal injury to healthy normal cells and tissues.

It is an additional object of the invention to provide such compositions that comprise one or more N-substituted 1-(1H) pyridone(s) and/or N-substituted 3-(1H) pyridone(s) as active anti-tumor ingredient(s).

Other objects of the present invention, as well as particular features and advantages thereof, will be elucidated in, or be apparent from, the following descriptions.

SUMMARY OF THE INVENTION

The present invention achieves the above objects, among others, and overcomes the limitations of the prior art by providing, [an] *in* a preferred embodiment, drugs having chemotherapeutic properties which are useful against certain neoplastic disorders with wide safety margins as evidenced by their low toxicity, and molecular actions. Such drugs include as active ingredient(s) one or more N-substituted 2-(1H) pyridone(s) and/or N-substituted 3-(1H) pyridone(s). The compositions of this invention are novel as anti-neoplastic drugs, namely as an agent for treating *malignant neoplasms* (*such as leukemias* [,] *and lymphomas, and/or benign neoplasms* (*such as leiomyomas*).

DETAILED DESCRIPTION OF THE PREFERRED EMBODIMENTS

Figure 1:
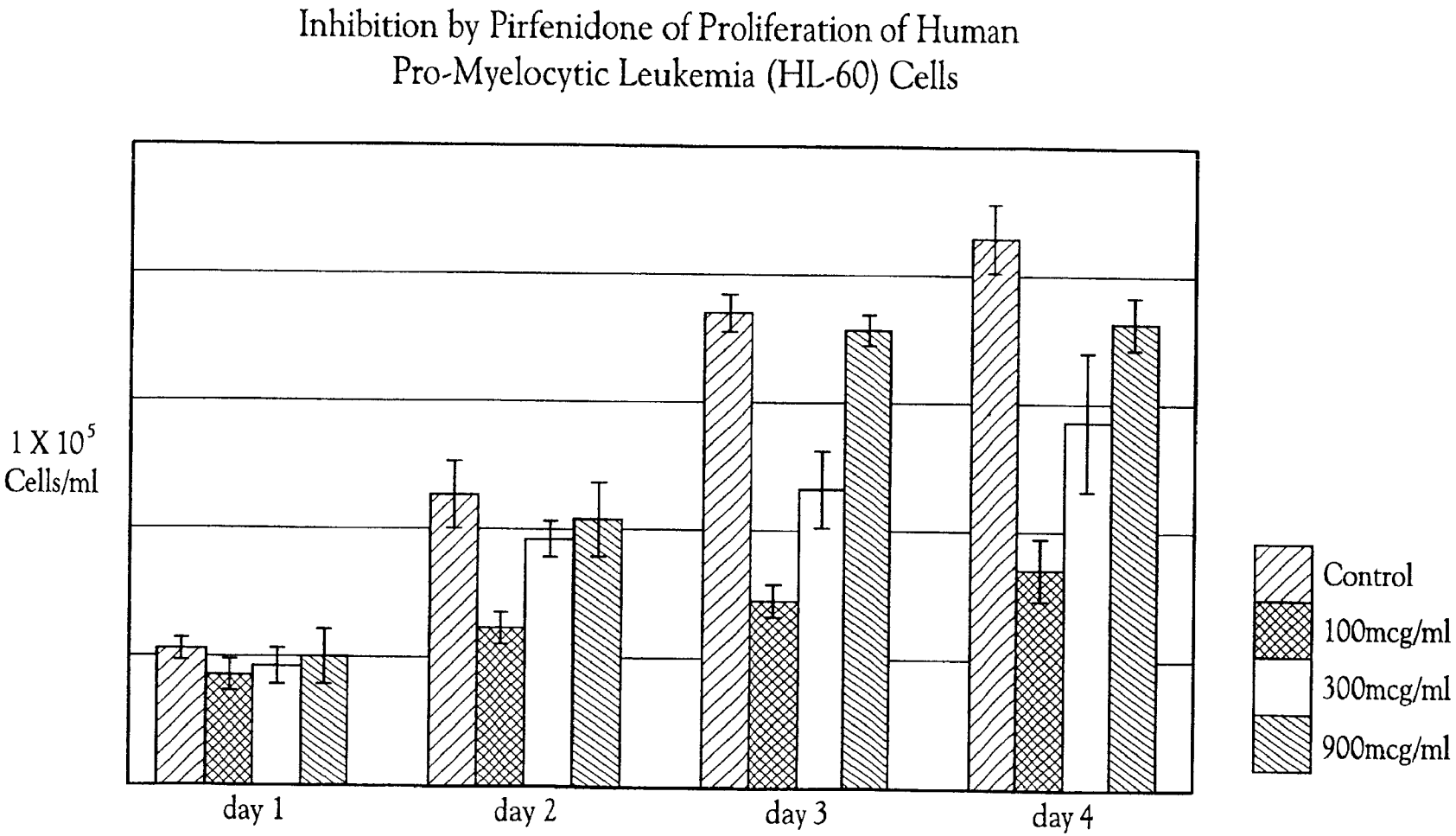
FIG. 1 is a bar graph showing the inhibition by pirfenidone of the proliferation of human pro-myelocytic leukemia cells.

Methods for Evaluating Anti-Cancer Agents in the Present Invention

All-trans-retinoic acid is known to specifically induce fresh human promyelocytic leukemia cells (AML3) to differentiate in vitro to mature functional gramulocytes which loose their self-renewal potency and spontaneously die. These results were confirmed in vivo: AML-3 patients treated with oral all-trans retinoic acid alone achieve complete remission (Chomienne, Ch., "Retinoids: Basic Sci. Clin. Appl.," 1994, p.233–241. Edited by Livrea and Vidali, Birkhaeuser, Basel, Switzerland).

Evidence that in vitro prednisolone resistance is of prognostic value in childhood acute lymphoblastic leukemia (ALL) was explored further in adult ALL leukemia. Blast cells from 30 patients were exposed to prednisolone (PDN) (0.1) microMol to 35 microMol), and cytotoxicity was assayed calorimetrically with soluble tetrazolium formazan (2,3-bis (2-methoxy-4-nitro-5-sulfophenyl)-5-[(phenylamino)carbamyl]-2H-tetrazolium hydroxide, XTT). The IC50 varied greatly among the samples from 0.3 microMol to >35 microMol. 15 microMol was subsequently chosen as IC50 cutoff between in vitro resistant and sensitive cases. By regression analysis, PDN-induced cytotoxicity was found to be significantly related to apoptosis. However, correlation with clinical symptoms was not demonstrated. Nevertheless, disease free survival was significantly better in sensitive patients (Tosi, P. et al., Eur. J. Haematology, 1996, 52:134–141.)

Chronic lymphocytic leukemia (CLL) is characterized by delayed senescence and a slow accumulation of small lymphocytes. Elevated cytokine levels have been detected in urine from patients with a variety of neoplastic diseases including various leukemias. The source of the elevated levels of cytokine has not been determined. In the present study, the intracellular cytokine level in lymphocytes from 36 patients with B-CLL and 15 normal donors was determined using an enzyme-lined immunoassay. In cells derived from patients with high risk disease, the median level of cytokine was 382 pg/200,000 cells compared to 91 pg/200,000 cells in patients with intermediate disease. In patients with low-risk disease, median cytokine level was 4.9 pg/200,000 cells, and in normal controls, it was 6.0 pg/200,000 cells. The respective differences were statistically significant (Menzel et al., Blood, 1996, 87:1056–1063).

In 1996, approximately 3,500 new cases (mostly children) of acute lymphoblastic leukemia (ALL) were diagnosed in the US. Current chemotherapy induces complete remission in many patients, but 20% suffer a critical relapse.

It has been discovered by the present inventor that pirfenidone and other N-substituted 2(1-H) pyridone compounds and N-substituted 3(1H) pyridone compounds have anti-tumor activity. Heretofore, before the discovery of the invention disclosed herein, no effective N-substituted pyridone agent or composition has been available for the inhibition and arrest of the growth, or for the destruction of mammalian benign or malignant tissues such as found in leukemias, lymphomas or leiomyomas.

The "anti-tumor" activity discovered by the present inventor and as used herein refers to the ability of an active substance to inhibit or arrest the life-threatening proliferation of neoplastic cells in *benign and malignant tumors including* lymphatic or hymelogenous leukemias, lymphomas, and leiomyomas.

Methods of preparation of some N-substituted 2(1-H) pyridones useful in the present invention are described in U.S. Pat. No. 3,839,346, issued Oct. 1, 1974, to Gadekar, and titled N-SUBSTITUTED PYRIDONE AND GENERAL METHOD FOR PREPARING PYRIDONES, the disclosure of which is incorporated by reference hereto.

EXAMPLE I

Inhibition of proliferation by pirfenidone of human promyelocytic leukemia (HL-60) cells in vitro.

Pirfenidone was suspended in RPMI, 2.0% FBS, at 100 micrograms to 900 micrograms per ml, and one other culture served as a control. Five ml of each pirfenidone concentration, and of the control were placed into a T25 tissue culture flask along with $1\times10^5$ cells. Every day for 4 days an aliquote from each flask was taken out, then stained with Trypan Blue, and counts were repeated three times on each aliquote.

The inhibition of proliferation of HL-60 cells by pirfenidone was directly related to the graded concentrations of pirfenidone in the respective culture flasks. After 3 and 4 days at a concentration of 900 micrograms/ml, a 63% pharmacologic inhibition was maintained without causing a toxic death of the cells (see FIG. 1). Inhibition of proliferation as well as deaths of almost all cells occur with pirfenidone concentrations at 1400 micrograms/ml.

EXAMPLE II

Inhibition of proliferation by pirfenidone of human T-cell leukemia (JURKAT) cells in vitro.

To determine the inhibitory effect of pirfenidone concentrations on human T-cell leukemia (JURKAT), a MTS assay was used which incorporates a tetrazolium dye that measures the cellular conversion of the dye into a formazan product by the activation of NADH-generating dehydrogenases found in metabolically active cells.

Procedure 1. 100 microl. of cells was seeded into 96 well plates at $1\times10^5$ cells/ml in media containing 100 mcg/ml, 300 mcg/ml and 900 mcg/ml of pirfenidone, as well as a pirfenidone-free media control.

2. Cells were incubated at 37 degrees C., at 5.0% CO2 for 72 hours.

3. After incubation a standard curve was made of 100 microliters of cells added to the plate at $5\times10^5$ cells/ml making 1:2 dilutions all the way down to a pre-set degree of dilution.

4. 2.0 mls of the MTS solution was mixed with a 100 microliter of the PMS solution, and 20 microliters of this combined dye solution was added to each well and incubated at 37 degrees C., 5.0% CO2 for 3 hours.

5. Subsequently the absorbance was read at 490 nm.

Figure 2:
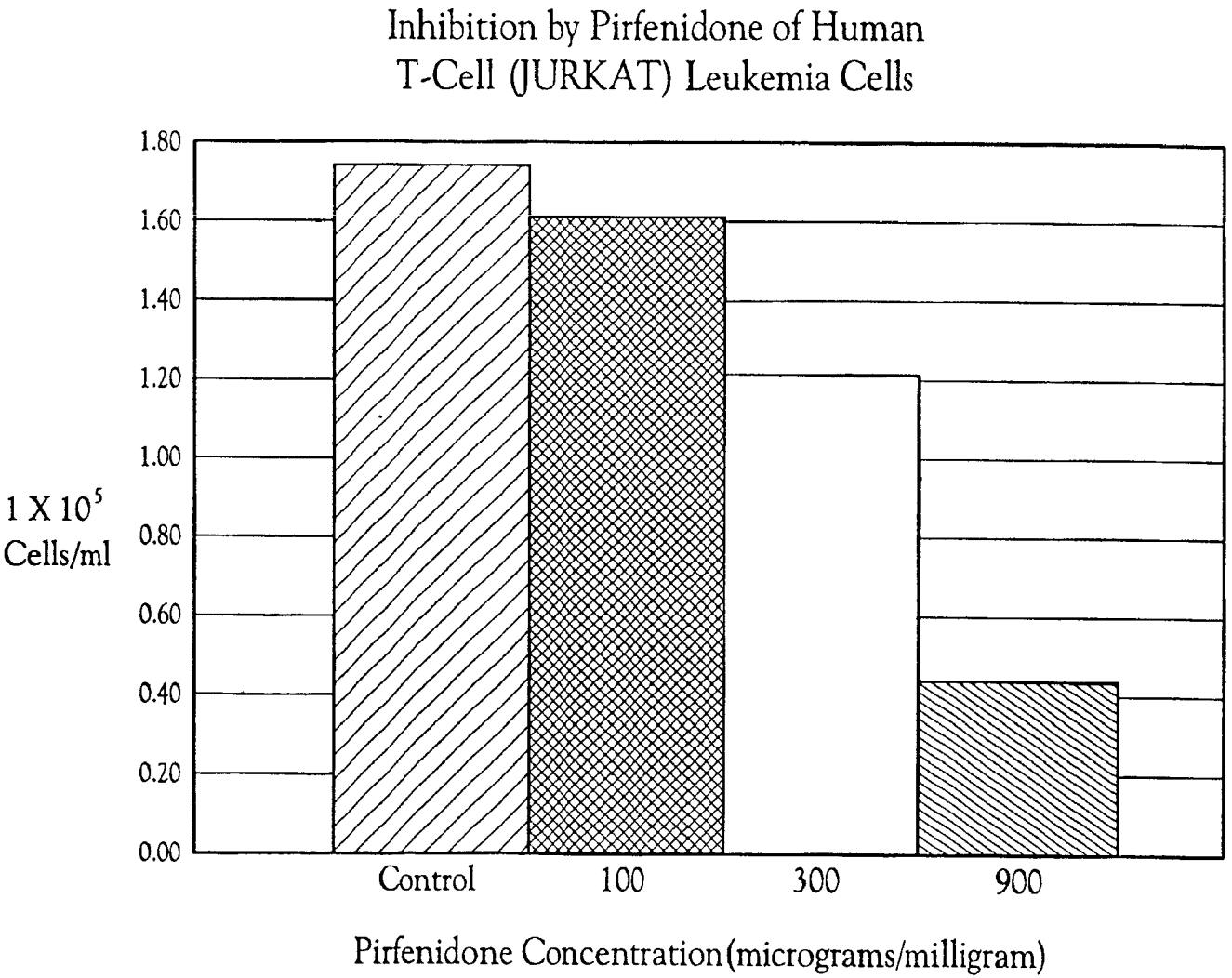
FIG. 2 is a bar graph showing the inhibition by prifenidone of human T-cell leukemia cells.

Exposure for only 72 hours of human T-cell leukemia (JURKAT) cells, at 900 mcg/ml of pirfenidone caused a statistically significant 75% reduction in number of cell which were active (75% no longer were able to proliferate; FIG. 2).

EXAMPLE III

Inhibition of proliferation by pirfenidone of human Burkitt's lymphoma (RAJI) cells in vitro.

To determine the inhibitory effect of pirfenidone concentrations on Burkitt's lymphoma (RAJI) cells, a MTS assay was used which incorporates a tetrazolium dye that measures the cellular conversion of the dye into a formazan product by the activation of NADH-generating dehydrogenases found in metabolically active cells.

Procedure 1. 100 microl. of cells was seeded into 96 well plates at $1\times10^5$ cells/ml in media containing 100 mcg/ml, 300 mcg/ml and 900 mcg/ml of pirfenidone, as well as a pirfenidone-free media control.

2. Cells were incubated at 37 degrees C., at 5.0% CO2 for 72 hours.

3. After incubation a standard curve was made of 100 microliters of cells added to the plate at $5\times10^5$ cells/ml making 1:2 dilutions all the way down to a pre-set degree of dilution.

4. 2.0 mls of the MTS solution was mixed with a 100 microliter of the PMS solution, and 20 microliters of this combined dye solution was added to each well and incubated at 37 degrees C., 5.0% CO2 for 3 hours.

5. Subsequently the absorbance was read at 490 nm.

Figure 3:
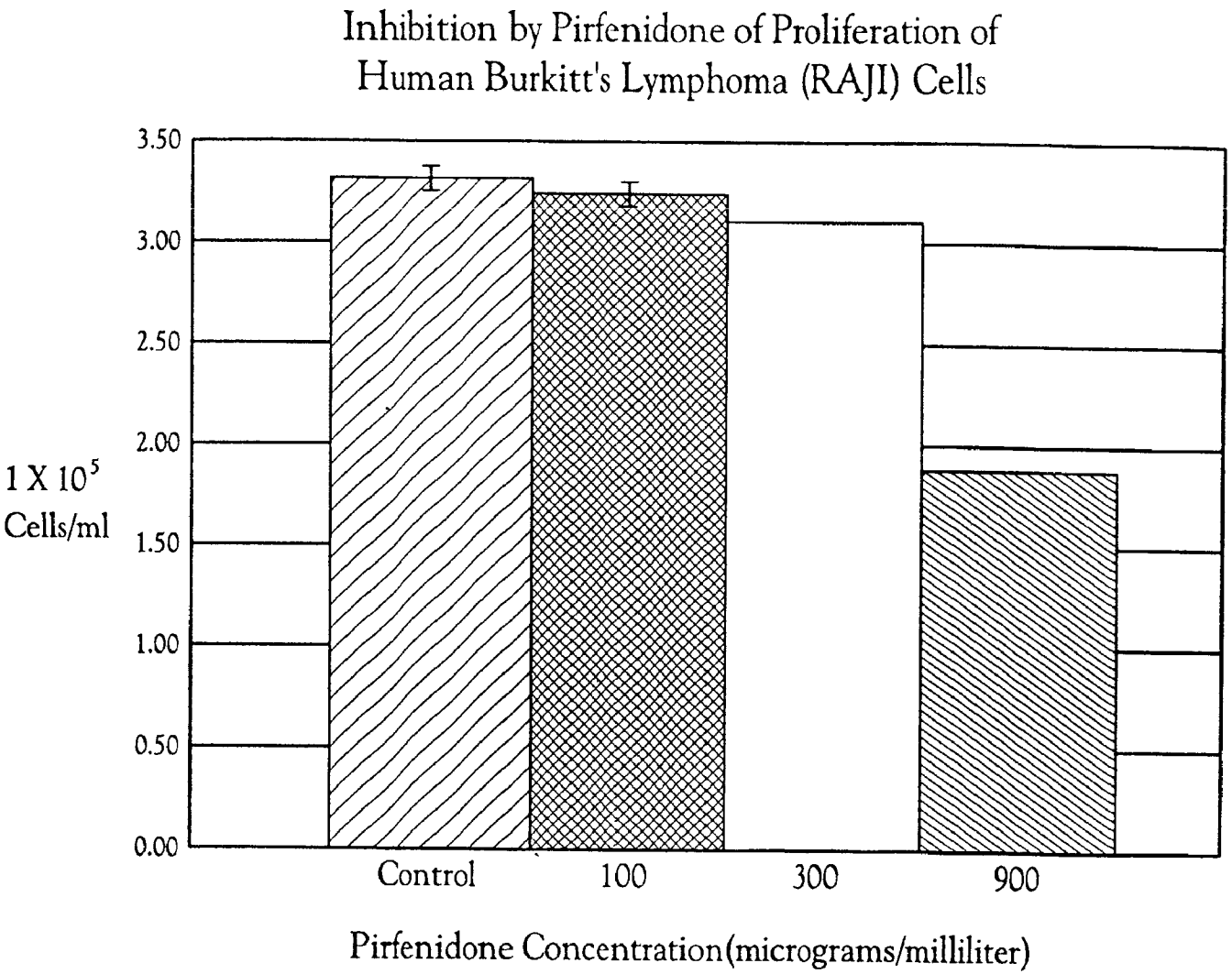
FIG. 3 is a bar graph showing the inhibition by pirfenidone of proliferation of human Burkitt's lymphoma cells.

Exposure for only 72 hours of these human Burkitt's lymphoma (RAJI) cells, at 900 mcg/ml of pirfenidone caused a statistically significant 45% reduction in number of cells which were active (45% no longer were able to proliferate; FIG. 3).

EXAMPLE IV

Leiomyoma tissues were obtained from several premenopausal women with symptomatic uterine fibroids at elective hysterectomy, and who were not receiving any hormonal or other drug therapy. The fibroid tissues were minced into 1–2 mm# explants and placed in suitable DMEM supplemented with 10% bovine serum. The fibroid tissue was digested for 14–18 hours at 37 degrees C. in an incubator. After centrifugation, a resulting cell pellet was resuspended in DMEM and then placed in culture flasks. The cultures were maintained at 37 degrees centigrade in a humidified atmosphere of 5% CO2 and 95% air.

For determining cell proliferation utilizing tritiated thymidine incorporation as an assay, leiomyoma cells were cultured in 96-well plates (15,000 cells/well) for 48 hours in DMEM plus 10.0% FBS serum. Cells were then made quiescent by culturing in DMEM plus 0.5% FBS serum for 48 hours. These quiescent cells were washed, and then placed in DMEM plus 10.0% FBS serum containing graded concentrations of pirfenidone (10.0, 100, 300 and 1000 micrograms/ml). After 18 hours, the cells received 0.2 uCi/well of [3H]-thymidine, and the incubation was continued for 6 more hours. Subsequently, cells were harvested and counted in a beta-counter to the rate of incorporation of [3H]-thymidine. Results are summarized in Table 1.

TABLE 1

INHIBITION BY PIRFENIDONE OF PROLIFERATION OF HUMAN LEIOMYOMA CELLS

| PIRFENIDONE TREATMENT (CONC/ML) | CELL COUNTS (DAY 7) LEIOMYOMA | RECENT DEAD CELLS (DAY 7) LEIOMYOMA |
|---|---|---|
| 0.0 MG | 380,000 | 9.0 |
| 0.01 MG | 315,000 | 8.0 |
| 0.1 MG | 205,000 | 10.0 |
| 0.3 MG | 170,000 | 6.0 |
| 1.0 MG | 69,000 | 16.0 |

EXAMPLE V

Leiomyoma cells were plated in 100 mm dishes (100,000 each dish) and allowed to attach overnight in DMEM plus 10% fetal bovine serum until they reached 80–90% confluence. The following day all cells received DMEM plus 10% fbs containing various concentrations of pirfenidone (0.0 micrograms, 100 micrograms, 300 micrograms or 1000 microgram/ml for seven (7) days. The medium was changed with addition of fresh treatments on days 3 and 5. On day 7, cells were harvested and counted. Cell viability was assessed using the Trypan Blue exclusive stain. Results are displayed in FIG. 4.

Figure 4:
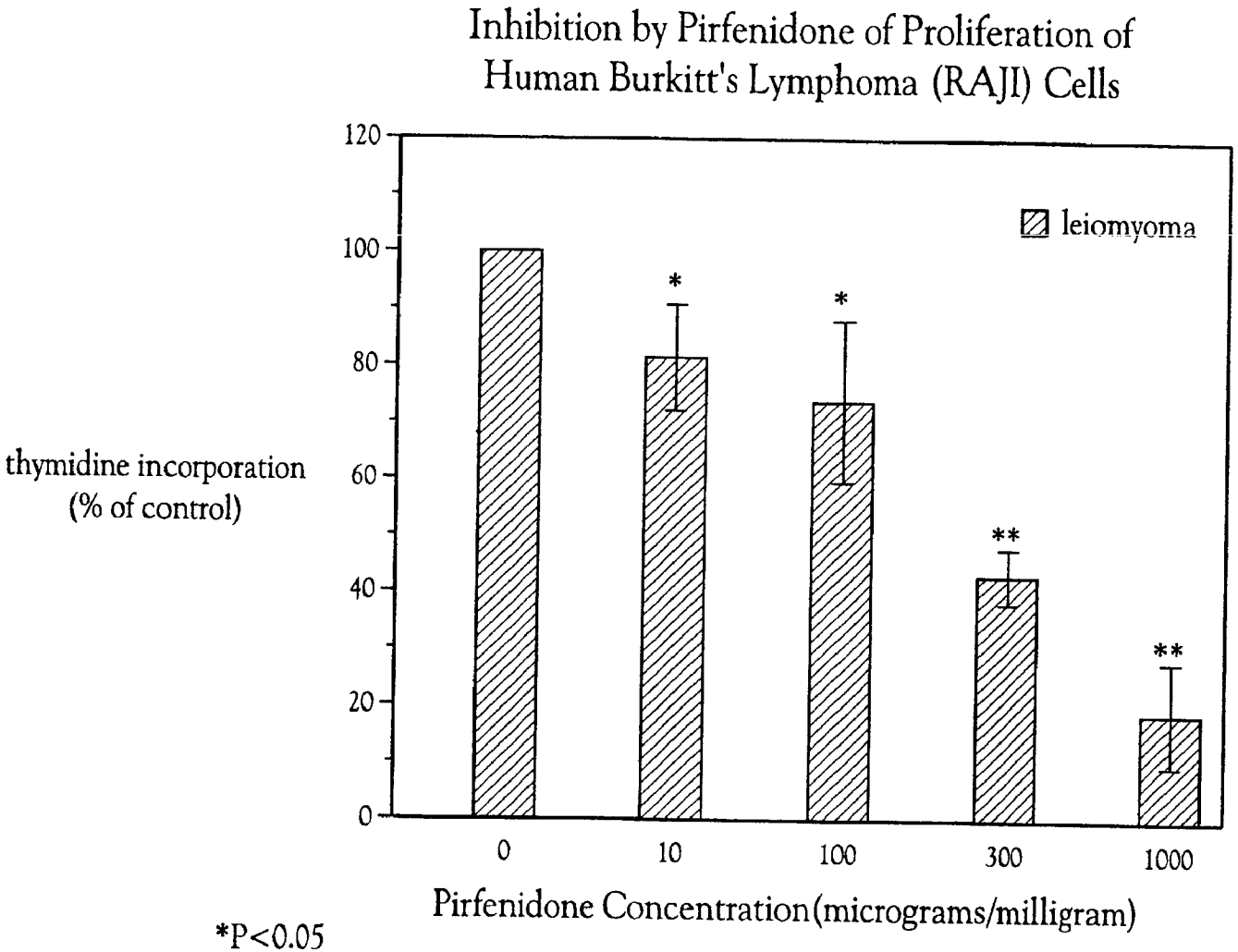
FIG. 4 is a bar graph showing the inhibition by pirfenidone of human leiomyoma cells.

A significant inhibitory effect on proliferation was seen for leiomyoma cells exposed to graded concentrations of pirfenidone in the culture media (FIG. 4). A significant increase in the percentage (16%) of dead leiomyoma cells was found at the 1000 micrograms/ml concentration of pirfenidone (Table 1).

The data demonstrates the anti-tumor effect [of] *on* leiomyomas [indicate] *indicates* that pirfenidone will be useful in eliminating the most severe symptoms associated with leiomyoma tumors (excessive abnormal arterial bleeding, pelvic pain, infertility and increased urinating frequency).

These compounds also can be employed in combination to enhance other types of therapy (surgery, radiation, immunotherapy or other chemotherapeutic compounds). Another facet of the present invention is absence of any severely debilitating adverse effects. The absence of such severe toxic reactions reduces or eliminates the patient discomfort inherent in conventional treatments for neoplasias. The delivery method to patients being treated may consist of oral, intramuscular or intravenous administration.

The N-substituted pyridones of the present invention pharmacologically arrest the proliferation of leukemias, Llymphomas, or leiomyoma cells or tissue, at concentrations that are ⅓rd–1/10th that which is toxic or killing to these neoplastic cells. Accordingly, this invention characterizes a group of chemotherapeutic compounds which provide a means of (1) arresting the proliferation and (2) then destroying the malignant cells by raising the pirfenidone concentration of the cell of tissue to the cytotoxic level or by adding another known cytotoxic anti-neoplastic agent, the neoplastic cells can be destroyed or eradicated without serious or fatal injury to healthy normal cells and tissues.

These compounds also can be employed in combination to enhance other types of therapy (surgery, radiation, immunotherapy or other chemotherapeutic compounds).

Another facet of the present invention is absence of any severely debilitating generalized adverse effects. The absence of such severe toxic reactions reduces or eliminates the patient discomfort inherent in conventional neoplasia treatments.

The differences in the concentrations of pirfenidone which pharmacologically arrest the proliferation of [neoplasia] *neoplastic* cells and the pirfenidone concentration which kills neoplasia cells affords a larger margin of safety for patients, (Raghu, G., et al., Amer. J. Resp. and Critical Care Med., 1997, Vol. 155:A741), and thereby distinctly reduces the incidence of serious adverse effects experienced by patients during treatment, as compared to treatment with currently conventional [anti-neoplasia] *anti-neoplastic* agents.

The intracellular action of pirfenidone in (1) arresting the proliferation and (2) subsequent destruction of the abnormal or neoplastic cells takes place in the cell nucleus and directly involves the signaling via the specific gene activated proteins (for example, p53, Rb, WT1, etc.) and ameliorating or blocking the impact of such gene proteins on the cell transcription apparatus and cyclins. These specific gene proteins act on the check points of the cell cycle to prevent or correct the aberrant gene protein signals impacting on the cyclins and check points.

It is estimated that the effective *human* dosage of one or more N-substituted 2-(1H) pyridone(s) and/or N-substituted 3-(1H) pyridone(s) in practicing the present invention is from about 250 to about 750 mg/kg of body weight per day, which dosage may be taken in the diet.

The general structural formula of N-substituted 2-(1H) pyridones is:

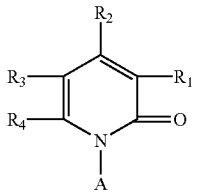

where: R1 is selected from the group consisting of (1) an alkyl group, with R3 hydrogen, and (2) hydrogen, with R3 consisting of an alkyl group; A is an aryl group; and R2 and R4 are hydrogen.

The general structural formula for the N-substituted 3-1 (H) pyridones is:

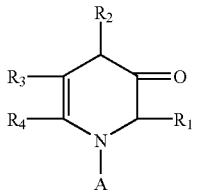

where: R2 is selected from the group consisting of (1) an alkyl group, with R3 hydrogen, and (2) hydrogen, with R3 consisting of an alkyl group; A is an aryl group; and R1 and R4 are hydrogen.

Examples of the pyridone compounds which have been found or are believed to be effective in practicing the present invention include:

5-Methyl-1-phenyl-2-(1H) pyridone
5-Methyl-1-(3-nitrophenyl-2)-(1H) pyridone
5-Methyl-1-(4'-methoxyphenyl)-2-(1H) pyridone
5-Methyl-1-p-tolyl-2-(1H) pyridone
5-Methyl-1-(3'-trifluoromethylphenyl)-2-(1H) pyridone
1-(4'Chlorophenyl)-5-methyl-2-(1H) pyridone
5-Methyl-1-(2'-naphthyl)-2-(1H) pyridone
5-Methyl-1-('-naphthyl)-2-(1H) pyridone
3-Methyl-1-phenyl-2-(1H) pyridone
6-Methyl-1-phenyl-2-(1H) pyridone
3,6-Dimethyl-1-phenyl-2-(1H) pyridone
5-Methyl-1-(2'thienyl)-2-(1H) pyridone
1-(2'-Furyl)-5-methyl-2-(1H) pyridone
5-Methyl-1-(5'-quinolyl)-2-(1H) pyridone
5-Methyl-1-(4'-pyridyl)-2-(1H) pyridone
5-Methyl-1-(3'-pyridyl)-2-(1H) pyridone
5-Methyl-1-(2'-pyridyl)-2-(1H) pyridone
5-Methyl-1-(2'-quinolyl)-2-(1H) pyridone
5-Methyl-1-(4'-quinolyl)-2-(1H) pyridone
5-Methyl-1-(2'-thiazolyl)-2-(1H) pyridone
1-(2'-Imidazolyl)-5-methyi-2-(1H) pyridone
5-Ethyl-1-phenyl-2-(1H) pyridone
3-Ethyl-1-phenyl-2-(1H) pyridone
1-Phenyl-2-(1H) pyridone
1-(4'-Nitrophenyl)-2(1H) pyridone
5-Methyl-3-phenyl-1-(2'-thienyl)-2-(1H) pyridone
5-Methyl-1-phenyl-3-(1H) pyridone
5-Methyl-1-(4'-methoxyphenyl)-3-(1H) pyridone
5-Methyl-1-p-tolyl-3-(1H) pyridone
1-(4'-Chlorophenyl)-5-methyl-3-(1H) pyridone
5-Methyl-1-(2'-naphthyl)-3-(1H) pyridone
4-Methyl-1-phenyl-3-(1H) pyridone
6-Methyl-1-pheyl-3-(1H) pyridone
5-Methyl-1-(2'-thienyl)-3-(1H) pyridone
1-(2'-Furyl)-5-methyl-3-(1H) pyridone
5-Methyl-1-(5'-quinolyl)-3-(1H) pyridone
5-Methyl-1-(3'-pyridyl)-3-(1H) pyridone
5-Methyl-1-(2'-pyridyl)-3-(1H) pyridone
5-Methyl-1-(2'-quinolyl)-3-(1H) pyridone
5-Ethyl-1-phenyl-3-(1H) pyridone
1-Phenyl-3-(1H) pyridone.

It will thus be seen that the objects set forth above, amoung those elucidated in, or made apparent from, the preceding description, are efficiently attained and, since certain changes may be made in the above compositions and methods without departing from the scope of the invention, it is intended that all matter contained in the foregoing disclosure shall be interpreted as illustrative only and not in a limiting sense.

It is also to be understood that the following claims are intended to cover all of the generic and specific features of the invention herein described and all statements of the scope of the invention which, as a matter of language, might be said to fall therebetween.

I claim:

1. A method of treating [lymphomas, leukemias, and/or leiomyomas] *one or more malignant tumors and/or one or more benign tumors* in a laboratory animal or a human, comprising: administering to said laboratory animal or said human an effective dose of a composition including one or more pharmaceutical substances selected from the group consisting of N-substituted 2-(1H) pyridones, N-substituted 3-(1) pyridones, and pharmaceutically acceptable salts thereof, wherein said 2-(1H) pyridones have the following general structural formula:

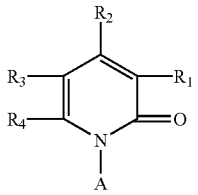

where: R1 is selected from the group consisting of (1) an alkyl group, with R3 hydrogen, and (2) hydrogen, with R3 consisting of an alkyl group; A is an aryl group; and R2 and R4 are hydrogen; and wherein said 3-(1H) pyridones have the following general structural formula:

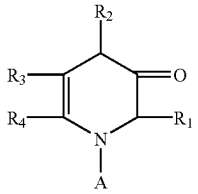

where: R2 is selected from the group consisting of (1) an alkyl group, with R3 hydrogen, and (2) hydrogen, with R3 consisting of an alkyl group; A is an aryl group; and R1 and R4 are hydrogen.

2. A method, as defined in claim 1, wherein: said composition is administered orally or parenterally to said laboratory animal at a rate of from about 250 to about 750 mg/kg of body weight per day.

3. A method, as defined in claim 1, wherein: said composition is administered orally or parenterally to [a] *said* human at a rate of from about 20 to about 60 mg/kg of body weight per day.

4. A method of treating [lymphomas, leukemias, and/or leiomyomas] *one or more malignant tumors and/or one or more benign tumors* in a laboratory animal or a human, comprising: administering to said laboratory animal or said human an effective dose of a composition including one or more pharmaceutical substances selected from the group consisting of N-substituted 2-(1H) pyridones, N-substituted 3-(1H) pyridones, and pharmaceutically acceptable salts thereof, said N-substituted 2-(1H) pyridones and said N-substituted 3-(1H) pyridones being selected from the group consisting of: 5-Methyl-1-phenyl-2-(1H) pyridone, 5-Methyl-1-(3-nitrophenyl-2)-(1H) pyridone, 5-Methyl-1-(4'-methoxyphenyl)-2-(1H) pyridone, 5-Methyl-1-p-tolyl-2-(1H) pyridone, 5-Methyl-1-(3'-trifluoromethylphenyl)-2-(1H) pyridone, 1-(4'Chlorophenyl)-5-methyl-2-(1H) pyridone, 5-Methyl-1-(2'-naphthyl)-2-(1H) pyridone, 5-Methyl-1-(1'-naphthyl)-2-(1H) pyridone, 3-Methyl-1-phenyl-2-(1H) pyridone, 6-Methyl-1-phenyl-2-(1H) pyridone, 3,6-Dimethyl-1-phenyl-2-(1H) pyridone, 5-Methyl-1-(2'thienyl)-2-(1H) pyridone, 1-(2'-Furyl)-5-methyl-2-(1H) pyridone, 5-Methyl-1-(5'-quinolyl)-2-(1H) pyridone, 5-Methyl-1-(4'-pyridyl)-2-(1H) pyridone, 5-Methyl-1-(3'-pyridyl)-2-(1H) pyridone, 5-Methyl-1-(2'-pyridyl)-2-(1H) pyridone, 5-Methyl-1-(2'-quinolyl)-2-(1H) pyridone, 5-Methyl-1-(4'-quinolyl)-2-(1H) pyridone, 5-Methyl-1-(2'-thiazolyl)-2-(1H) pyridone, 1-(2'-Imidazolyl-5-methyl-2-(1H) pyridone, 5-Ethyl-1-phenyl-2-(1H) pyridone, 3-Ethyl-1-phenyl-2-(1H) pyridone, 1-Phenyl-2-(1H) pyridone, 1-(4'-Nitrophenyl)-2-(1H) pyridone, 5-Methyl-3-phenyl-1-(2'-thienyl)-2-(1H) pyridone, 5-Methyl-1-phenyl-3-(1H) pyridone, 5-Methyl-1-(4'-methoxyphenyl)-3-(1H) pyridone, 5-Methyl-1-p-tolyl-3-(1H) pyridone, 1-(4'-Chlorophenyl)-5-methyl-3-(1H) pyridone, 5-Methyl-1-(2'-naphthyl)-3-(1H) pyridone, 4-Methyl-1-phenyl-3-(1H) pyridone, 6-Methyl-1-phenyl-3-(1H) pyridone, 5-Methyl-1-(2'-thienyl)-3-(1H) pyridone, 1-(2'-Furyl)-5-methyl-3-(1H) pyridone, 5-Methyl-1-(5'-quinolyl)-3-(1H) pyridone, 5-Methyl-1-(3'-pyridyl)-3-(1H) pyridone, 5-Methyl-1-(2'-pyridyl)-3-(1H) pyridone, 5-Methyl-1-(2'-quinolyl)-3-(1H) pyridone, 5-Ethyl-1-phenyl-3-(1H) pyridone, and 1-Phenyl-3-(1H) pyridone.

* * * * *